United States Patent [19]

Wenander

[11] 4,037,464
[45] July 26, 1977

[54] DEVICE FOR TRANSFERRING BLOOD OR A SIMILAR FLUID TO A PIPETTE

[75] Inventor: Björn Wenander, Saro, Sweden

[73] Assignee: Mediplast AB, Molndal, Sweden

[21] Appl. No.: 584,163

[22] Filed: June 5, 1975

[30] Foreign Application Priority Data

June 24, 1974 Sweden .................... 7408222

[51] Int. Cl.² .................... G01N 1/14; G01N 33/16
[52] U.S. Cl. .................... 73/61.4; 23/259;
73/425.4 P; 128/272
[58] Field of Search ............... 73/425.4 P, 425.6, 61.4;
23/259; 210/359, DIG. 23, DIG. 24; 128/2 F, DIG. 5; 141/29, 21

[56] References Cited

U.S. PATENT DOCUMENTS

| | | | |
|---|---|---|---|
| 3,481,477 | 12/1969 | Farr | 210/359 |
| 3,590,889 | 7/1971 | Vannus | 73/425.4 P |
| 3,814,079 | 6/1974 | LeRoy, Sr. | 210/359 |
| 3,827,286 | 8/1974 | Bond et al. | 73/425.4 P |
| 3,832,141 | 8/1974 | Haldopoulos | 23/259 X |
| 3,834,876 | 9/1974 | Kormendy et al. | 73/425.4 P X |
| 3,850,174 | 11/1974 | Ayres | 210/DIG. 23 |

Primary Examiner—Richard C. Queisser
Assistant Examiner—Daniel M. Yasich

[57] ABSTRACT

A hygienic and contamination-free transfer of blood or corresponding fluids from a cylindrical collecting container, such as a test tube, to a pipette is most desirable for instance at determination of the sedimentation rate of the blood corpuscles; the invention concerns a device for accomplishing such a transfer comprising in combination a tube formed pipette of a compressible, transparent material, a cylindrical body designed to cooperate with the interior of the container as a piston/cylinder arrangement; the cylindrical body being provided at one end of the tube and having an axial through hole adapted to allow communication between the tube and the container.

4 Claims, 5 Drawing Figures

DEVICE FOR TRANSFERRING BLOOD OR A SIMILAR FLUID TO A PIPETTE

FIELD OF THE INVENTION

The invention relates generally to apparatus used for transferring blood or similar fluids from a collecting container to a pipette for determining sedimentation rate of blood corpuscles, or the like.

BACKGROUND OF THE INVENTION

When determining the sedimentation rate of blood corpuscles the blood is mixed with a citrate solution, after which the mixture is transferred to a pipette to a certain level, whereupon the pipette is placed in a stand. The transfer of the blood-citrate mixture can be made in different ways, e.g. by using the pipette as a suction pipe or by putting the pipette into a certain container, so designed that the pipette acts as a piston therein. In both these methods, the blood must be transferred from the blood sample syringe to a second vessel or container, from which the blood-citrate mixture is transferred to the pipette. Thus it is necessary to use several means and the risk of contamination during transfer is obvious. When transferring blood from such a container, where the pipette acts as a piston, it can occur that when the blood pillar has reached the determined level in the pipette, but the end of the pipette has not been pushed right down to the bottom of the container, that the blood pillar actually is so much longer than the blood quantity left in the container, whereby misleading readings are obtained. To an ever increasing extent blood samples are now taken according to the vacuum blood system, i.e. by using essentially evacuated containers provided with a sealing rubber stopper, which is punctured with a cannula with puncture tips at both ends, and where the vacuum in the container is utilized for sucking up a certain quantity of blood. The system offers a direct transfer of blood from the patients vein to a hermetically closed test tube, in which the citrate solution is contained. The risk of contamination of the blood and transmission of infection during the sampling and transport of the test tube to the laboratory is thereby avoided. Under strict security regulations, the rubber stopper of the test tube is removed in the laboratory and the transfer of blood to the pipette is done in conventional way, usually by using the pipette as a suction pipe, which is then dipped under the blood level in the test tube. The pipette with the blood pillar shall thereafter be moved to a stand with the risk of spillage and contamination. This system consequently solves the problem at the blood sampling only, but the above mentioned disadvantages of the transfer to the pipette for sedimentation reaction continue to exist.

SUMMARY OF THE INVENTION

The purpose of the present invention is first to be able to utilize the hygienic and practical advantages offered by the vacuum system, and second to suggest a transfer system, which is simple and time-saving, which requires no additional vessels, and during the transfer, the risk of contamination of the blood and the transmission of infection are reduced to nil. This problem is solved by a device comprising a pipette designed as a compressible, transparent tube provided at one of its ends with a cylindrical body having an axial through-channel communicating with the tube, said cylindrical body being designed to slidingly fit as a piston into the cylindric collecting container. According to a further development of the invention, it is possible to transfer blood from the vacuum tube without breaking its seal, whereby the risk of contamination is practically nil.

DESCRIPTION OF THE PREFERRED EMBODIMENTS

Figure 1:
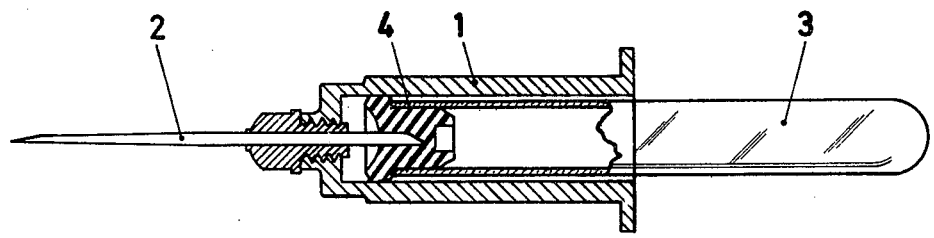
FIG. 1 shows a section through a conventional vacuum system device for blood sampling.
Figure 2:
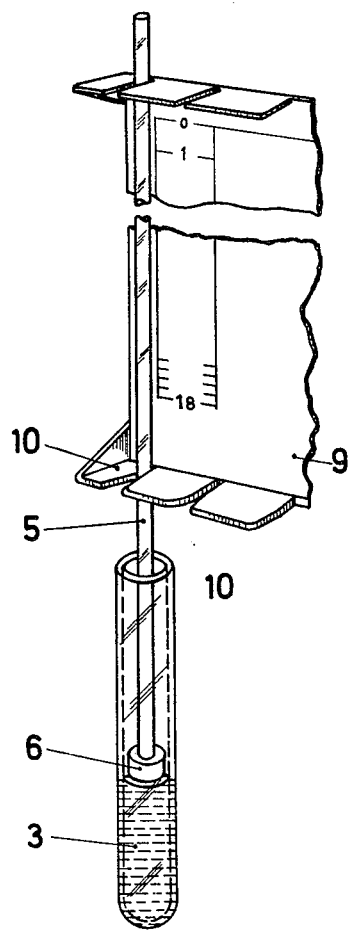
FIG. 2 shows, in perspective, a part of a stand for determination of the sedimentation rate and holding a pipette provided with the device according to the invention.
Figure 3:
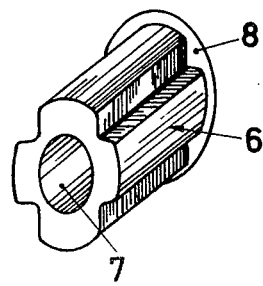
FIG. 3 shows in enlarged perspective, the piston according to the invention.
Figure 4:
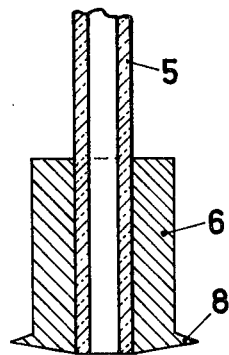
FIG. 4 shows a section through the piston and part of the pipette.
Figure 5:
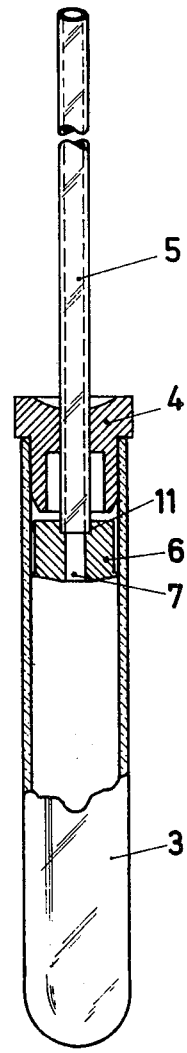
FIG. 5 shows a section through a modified embodiment of the invention.

At blood sampling, according to the vacuum system, a cannula casing 1 is used, which at one end is provided with an attachment for a cannula 2 provided at both ends with puncture tips. A test tube 3 can be inserted into the casing 1, the end of the tube introduced into the casing being closed by a rubber stopper 4. At blood sampling the vein is punctured by the outer tip of the cannula 2 while its inner tip is used for puncturing the rubber stopper 4. A certain quantity of citrate solution is enclosed in the test tube 3 and the vacuum in the tube will cause blood to be sucked into it when a vein is punctured. When the test tube 3 is drawn out of the cannula casing 1, the rubber stopper automatically closes the opening after the cannula tip and a hermetical closure is obtained. The blood-citrate mixture is transferred to a pipette for determination of the sedimentation rate by means of a pipette tube 5, which at one end is provided with a piston 6 displaceably fitting inside the cylindrical test tube 3. The piston is provided with an axial through channel 7 wherein the pipette tube 5 is insertable. The pipette tube can be held in the channel 7 by friction or it can be connected with it in any suitable way, for example, by glueing. It is also possible to design the tube and the piston in one piece. For manufacturing reasons, it can be preferable to give the piston a cross-formal, cross section and to provide it at one end with a circular part 8 with slightly larger diameter than the inner diameter of the test tube 3. The transfer of mixture from the test tube 3 to the pipette 7 is accomplished by removing the stopper 4 under adequate sterile conditions from the tube, and the tube, which, for instance, is taken from a sterile package is attached at its upper part to a stand 9. The test tube, with blood, is moved vertically up against the piston of the pipette, whereby a blood pillar (column) is pressed up into the pipette tube 5 and when the blood has reached a desired level, noted on the stand, the pipette tube is attached to the lower part of the stand in locking tongues 10 (only some of the lower locking tongues of the stand are shown) and the pipette tube is squeezed between these locking tongues, so that the tube is closed. The blood pillar located above the squeezing point thereby will have an exact length and volume for accomplishing the sedimentation reaction, while the blood quantity located below the squeezing point will take no part in the reaction. After the reaction has been accomplished both the pipette tube and test tube 3 can be thrown away as a unit. The new piston-provided pipette tube thus offers a direct transfer of blood from a blood sampling tube without the need of transferring the blood to an additional intermediate container, whereby the risk of contamination is considerably reduced. It has been made possible to utilize the advantages of the vacuum system with very simple means at the same time as the available wall stands in laboratories and hospital departments can be used. In order to attain a system which is maintained completely closed from the blood sampling until the sedimentation reaction, the device according to FIG. 5 is used. The piston 6, according to this embodiment, is located in the test tube 3 inside the stopper 4. The stopper and the piston can be made of the same material and may be interconnected by very thin, easily breakable parts possibly provided with fracture-lines. The channel 7 in the piston 6 has a slightly smaller diameter than the external diameter of the pipette tube, and at the end of the piston turned towards the stopper the channel 7 is provided with a widened portion 11 intended to take up one end of the pipette tube. The widened portion 11 as well as the end of the pipette tube can be made tapering in order to facilitate the introduction of the pipette through the stopper and also to improve the sealing of the piston. After blood sampling has been carried out with the cannula casing shown in FIG. 1, the transfer of blood-citrate mixture is brought about by pressing the pipette tube into the stopper opening caused by the cannula, until the end of the pipette tube abuts the piston 6. By continued displacement of the pipette tube into the test tube, the piston will be pressed down into the test tube and the mixture is pressed up into the pipette tube. The pipette tube and the test tube fitted thereto are then attached to the stand 9 and the sedimentation reaction can be started. The blood sampling, the transport to the laboratory, and the transfer of blood to the sedimentation pipette can take place under hermetically sealed conditions due to the fact that the piston is positioned directly in the test tube and while the system is a logical development of the conventional method, without complicated equipment and greater costs of investment the method can be carried through by less experienced personnel, and the device may be manufactured as a non-recurring (disposable) article. The device according to the invention can also be used for other purposes, e.g. for transferring, without spilling a liquid from one test tube to another vessel.

What I claim is:

1. An improved expendable assembly for transfer of blood, comprising a test tube and a pipette for determination of the sedimentation rate of a blood sample, said pipette including a compressible, transparent tube provided at one end with a cylindrical body having an axial through-channel communicating with the pipette, said cylindrical body forming a piston slidingly accommodated in the test tube so that blood is caused to rise in the to a predetermined level by displacing the piston downward into the test tube, and a stand provided with at least two upper and lower vertically spaced series of locking tongues arranged, after the pipette is filled, to secure the pipette in a vertical position by pinching said compressible pipette tube between two adjacent tongues in each one of said spaced-apart series of locking tongues, thereby pinching the pipette tube so as to give the pipette said sample of blood isolated from the interior of the test tube so that determination of the sedimentation rate of the blood sample can be accomplished.

2. The structure as claimed in claim 1 wherein the piston is detachably connected to the pipette.

3. The structure as claimed in claim 1 in which said piston and pipette comprise a one-piece unit.

4. A system for transferring blood from a test tube to a pipette for determination of the sedimentation rate of the blood comprising an elastic stopper hermetically closing said test tube, said stopper being elastically-sealable and cooperating with a puncturing cannula having a puncture tip at one end for puncturing a vein when a blood sample is being taken, and said cannula having a puncture tip at the other end for puncturing the elastic stopper, said pipette comprising a compressible, transparent tube, a cylindrical body telescopically-received in the test tube, beneath the stopper, said cylindrical body having an axial through-channel and functioning as a piston in the test tube, the stopper being removable and penetratable by the pipette after removal of the cannula, the channel of the piston having at its inner end a portion accommodating the pipette so that blood will rise in the pipette to a desired level by displacing the piston into the test tube, said pipette being securable in a vertical position in a retention stand provided with upper and lower series of locking tongues, arranged to retain said pipette between two adjacent tongues in each of said upper and lower series of locking tongues and thereby also compressing said compressible pipette tube to prevent communication with the interior of said test tube, so that a predetermined sample can be examined for the sedimentation rate of the blood contained in the pipette.

* * * * *